(12) United States Patent
Lagree

(10) Patent No.: US 10,016,655 B2
(45) Date of Patent: *Jul. 10, 2018

(54) EXERCISE MACHINE ADJUSTABLE RESISTANCE SYSTEM AND METHOD

(71) Applicant: Lagree Technologies, Inc., Burbank, CA (US)

(72) Inventor: Sebastien Anthony Louis Lagree, Burbank, CA (US)

(73) Assignee: Lagree Technologies, Inc., Burbank, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,521

(22) Filed: Oct. 2, 2017

(65) Prior Publication Data

US 2018/0056133 A1 Mar. 1, 2018

Related U.S. Application Data

(63) Continuation of application No. 15/588,953, filed on May 8, 2017, now Pat. No. 9,776,043, which is a continuation of application No. 15/450,001, filed on Mar. 5, 2017, now Pat. No. 9,643,051, which is a (Continued)

(51) Int. Cl.
*A63B 21/04* (2006.01)
*A63B 24/00* (2006.01)

(52) U.S. Cl.
CPC ................... *A63B 24/0075* (2013.01)

(58) Field of Classification Search
CPC ............ A63B 24/0075; A63B 21/0051; A63B 21/0428; A63B 21/0052; A63B 22/203; A63B 71/0619; A63B 21/023; A63B 24/0062; A63B 24/0087; A63B 2230/062; A63B 2071/065; A63B 2225/50;

(Continued)

(56) References Cited

U.S. PATENT DOCUMENTS

| | | | |
|---|---|---|---|
| 3,770,267 A | 11/1973 | Mccarthy | |
| 4,013,068 A | 3/1977 | Settle | |
| 5,066,005 A | 11/1991 | Luecke | |

(Continued)

FOREIGN PATENT DOCUMENTS

WO    WO 2014084742    6/2014

OTHER PUBLICATIONS

TERA Fitness Mat; Jun. 8, 2014; Lunar Europe; http://tera.lunar-europe.com.
Iphone free App (Dec. 16, 2010) Finger Balance; tuuske; Dec. 16, 2010; Youtube; https://www.youtube.com/watch?v=xj2xuGsB3yo.
http://www.brainproducts.com/productdetails.php?id=63&tab=1; Live Amp Overview; Received and Printed Jun. 14, 2016.
http://www.brainproducts.com/productdetails.php?id=63&tab=1; LiveAmp Overview; Received and Printed Jun. 14, 2016.

(Continued)

*Primary Examiner* — Garrett Atkinson
(74) *Attorney, Agent, or Firm* — Neustel Law Offices

(57) ABSTRACT

An exercise machine adjustable resistance system and method for efficiently varying the workout resistance for an exercise machine. The exercise machine adjustable resistance system and method generally includes a control unit in communication with a resistance adjustment system of an exercise machine and a biometric monitoring device used by an exerciser on the exercise machine. The control unit receives biometric data from the biometric monitoring device and sends a control signal to the resistance adjustment system to adjust the resistance of the exercise machine based on the biometric data received.

20 Claims, 9 Drawing Sheets

Related U.S. Application Data continuation of application No. 14/742,144, filed on Jun. 17, 2015, now Pat. No. 9,586,089.

(60) Provisional application No. 62/013,032, filed on Jun. 17, 2014.

(58) Field of Classification Search
CPC .......... A63B 2024/0093; A61B 5/6895; A61B 5/024; A61B 5/4836
USPC ... 482/72, 73, 121, 122, 129, 130, 133, 135, 482/138
See application file for complete search history.

(56) References Cited

U.S. PATENT DOCUMENTS

| | | | |
|---|---|---|---|
| 5,201,694 A * | 4/1993 | Zappel | A63B 21/00072 482/133 |
| 5,365,934 A | 11/1994 | Leon | |
| 5,738,104 A | 4/1998 | Lo | |
| 5,812,978 A | 9/1998 | Nolan | |
| 6,152,856 A | 11/2000 | Studor | |
| 7,108,635 B2 | 9/2006 | Howlett-Campanella | |
| 7,163,500 B2 | 1/2007 | Endelman | |
| 7,192,387 B2 | 3/2007 | Mendel | |
| 7,448,986 B1 | 11/2008 | Porth | |
| 7,537,554 B2 * | 5/2009 | Zhuang | A63B 21/023 482/121 |
| 7,803,095 B1 * | 9/2010 | LaGree | A63B 22/0089 482/121 |
| 7,914,420 B2 | 3/2011 | Daly | |
| 7,967,728 B2 * | 6/2011 | Zavadsky | A63B 21/00 434/247 |
| 8,287,434 B2 * | 10/2012 | Zavadsky | A63B 21/00 482/1 |
| 8,303,470 B2 * | 11/2012 | Stewart | A63B 22/001 482/51 |
| 8,641,585 B2 * | 2/2014 | LaGree | A63B 21/023 482/92 |
| 8,812,075 B2 | 8/2014 | Nguyen | |
| 8,852,062 B2 * | 10/2014 | Dorsay | A63B 23/1209 482/121 |
| 8,911,328 B2 | 12/2014 | Alessandri | |
| 9,011,291 B2 * | 4/2015 | Birrell | A63B 71/0622 482/1 |
| 9,199,123 B2 * | 12/2015 | Solow | A63B 26/00 |
| 2002/0137607 A1 * | 9/2002 | Endelman | A63B 21/023 482/123 |
| 2003/0119635 A1 | 6/2003 | Arbuckle | |
| 2006/0183606 A1 * | 8/2006 | Parmater | A63B 22/0076 482/72 |
| 2007/0202992 A1 * | 8/2007 | Grasshoff | A63B 21/0058 482/8 |
| 2007/0224582 A1 | 9/2007 | Hayashino | |
| 2007/0270293 A1 * | 11/2007 | Zhuang | A63B 21/023 482/123 |
| 2008/0051256 A1 | 2/2008 | Ashby | |
| 2008/0058174 A1 | 3/2008 | Barnard | |
| 2008/0139975 A1 | 6/2008 | Einav | |
| 2008/0242519 A1 * | 10/2008 | Parmater | A63B 22/0076 482/72 |
| 2009/0005698 A1 | 1/2009 | Lin | |
| 2009/0291805 A1 | 11/2009 | Blum | |
| 2009/0312152 A1 | 12/2009 | Kord | |
| 2010/0125026 A1 * | 5/2010 | Zavadsky | A63B 21/00 482/5 |
| 2010/0227748 A1 | 9/2010 | Campanaro | |
| 2010/0267524 A1 * | 10/2010 | Stewart | A63B 22/001 482/52 |
| 2011/0018233 A1 | 1/2011 | Senner | |
| 2011/0077127 A1 | 3/2011 | Ishii | |
| 2011/0152045 A1 * | 6/2011 | Horne | A63B 24/0062 482/131 |
| 2011/0172069 A1 | 7/2011 | Gerschefske | |
| 2011/0184559 A1 | 7/2011 | Benabid | |
| 2012/0015334 A1 | 1/2012 | Hamilton | |
| 2012/0088634 A1 | 4/2012 | Heidecke | |
| 2012/0143020 A1 | 6/2012 | Bordoley | |
| 2012/0190505 A1 | 7/2012 | Shavit | |
| 2012/0202656 A1 * | 8/2012 | Dorsay | A63B 21/156 482/121 |
| 2012/0228385 A1 | 9/2012 | DeLuca | |
| 2012/0295771 A1 * | 11/2012 | LaGree | A63B 21/023 482/94 |
| 2013/0072353 A1 | 3/2013 | Alessandri | |
| 2013/0196835 A1 * | 8/2013 | Solow | A63B 26/00 482/142 |
| 2013/0210578 A1 * | 8/2013 | Birrell | A63B 71/0622 482/4 |
| 2013/0289889 A1 | 10/2013 | Yuen | |
| 2014/0011645 A1 | 1/2014 | Johnson | |
| 2014/0066257 A1 | 3/2014 | Shavit | |
| 2014/0121076 A1 * | 5/2014 | Lagree | A63B 21/0552 482/123 |
| 2014/0121078 A1 | 5/2014 | Lagree | |
| 2014/0141948 A1 | 5/2014 | Aronson | |
| 2014/0148715 A1 | 5/2014 | Alexander | |
| 2014/0213415 A1 | 7/2014 | Parker | |
| 2015/0012111 A1 | 1/2015 | Contreras-Vidal | |
| 2015/0024914 A1 | 1/2015 | Lagree | |
| 2015/0057127 A1 | 2/2015 | Lagree | |
| 2015/0065318 A1 | 3/2015 | Lagree | |
| 2015/0072841 A1 | 3/2015 | Lagree | |
| 2015/0105223 A1 | 4/2015 | Bissu | |
| 2015/0141204 A1 | 5/2015 | Lagree | |
| 2015/0217164 A1 | 8/2015 | Lagree | |
| 2015/0220523 A1 | 8/2015 | Lagree | |
| 2015/0297944 A1 | 10/2015 | Lagree | |
| 2015/0343250 A1 | 12/2015 | Lagree | |
| 2015/0360068 A1 | 12/2015 | Lagree | |
| 2015/0360083 A1 | 12/2015 | Lagree | |
| 2015/0360113 A1 | 12/2015 | Lagree | |
| 2015/0364058 A1 | 12/2015 | Lagree | |
| 2015/0364059 A1 | 12/2015 | Marks | |
| 2015/0367166 A1 | 12/2015 | Lagree | |
| 2016/0008657 A1 | 1/2016 | Lagree | |
| 2016/0059060 A1 | 3/2016 | Lagree | |
| 2016/0059061 A1 | 3/2016 | Lagree | |
| 2016/0096059 A1 | 4/2016 | Lagree | |
| 2016/0271452 A1 | 9/2016 | Sebastien Anthony Louis Lagree | |

OTHER PUBLICATIONS http://www.cognionics.com/index.php/products/hd-eeg-systems/72-channel-system; Cognionics HD-72 Overview; Received and Printed Jun. 14, 2016.
http://www.cognionics.com/index.php/products/hd-eeg-systems/quick-20-dry-headset; Cognionics Quick-20 Dry EEG Headset; Received and Printed Jun. 14, 2016.
http://www.cognionics.com/index.php/products/mini-systems/multi-position-dry-headband; Cognionics Multi-Position Dry EEG Headband; Received and Printed Jun. 14, 2016.
http://www.cognionics.com/index.php/products/mini-systems/dry-eeg-headband; Cognionics Dry EEG Headband; Received and Printed Jun. 14, 2016.
http://www.cognionics.com/index.php/products/hd-eeg-systems/mobile-eeg-cap; Cognionics Mobile-72 Wireless EEG System; Received and Printed Jun. 14, 2016.
PCT International Search and Opinion from International Searching Authority for PCTUS2017041638; dated Sep. 28, 2017.
PCT Preliminary Report on Patentability from International Searching Authority for PCTUS2016022888; dated Sep. 28, 2017.
PCT International Search and Opinion from International Searching Authority for PCTUS2016022888 dated Jul. 25, 2016.

* cited by examiner

EXERCISE MACHINE ADJUSTABLE RESISTANCE SYSTEM AND METHOD

CROSS REFERENCE TO RELATED APPLICATIONS

The present application is a continuation of U.S. application Ser. No. 15/588,953 filed on May 8, 2017 which issues as U.S. Pat. No. 9,776,043 on Oct. 3, 2017, which is a continuation of U.S. application Ser. No. 15/450,001 filed on Mar. 5, 2017 now issued as U.S. Pat. No. 9,643,051, which a continuation of U.S. application Ser. No. 14/742,144 filed on Jun. 17, 2015 now issued as U.S. Pat. No. 9,586,089, which claims priority to U.S. Provisional Application No. 62/013,032 filed Jun. 17, 2014. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND OF THE INVENTION

Field of the Invention

The present invention relates generally to an exercise machine and more specifically it relates to an exercise machine adjustable resistance system and method for efficiently varying the workout resistance for an exercise machine.

Description of the Related Art

Any discussion of the related art throughout the specification should in no way be considered as an admission that such related art is widely known or forms part of common general knowledge in the field.

Contemporary Pilates apparatuses are well known throughout the fitness industry, and are generally comprised of a rectangular frame supported on the floor at various points of contact about the rectangular frame.

The base structure of a Pilates apparatus supports an upper structure comprised of two parallel rails aligned with the major length axis of the rectangular structure, and a slidable carriage thereupon that is attached to one end of the structure by springs or elastic bands that produce a resistance bias on the slidable carriage.

Exercises are performed by an exerciser by moving the slidable carriage along the rails in a direction distal to the end of the apparatus to which the fixed end of the resistance springs are attached. One or more resistance springs create a workload against which therapeutic or fitness exercises can be safely and beneficially performed.

Traditional Pilates apparatuses typically provide for a plurality of spring assemblies that may be removably attached between the slidable carriage and the fixed end, with each spring being of a specified design to deliver a known force. As an example, six resistance springs, each delivering a constant K-factor of 15 pounds, may be installed on an apparatus. An exerciser therefore would engage one of the springs in order to perform arm exercises against a 15 pound resistance force.

When the exerciser changes exercises to leg exercises, the exerciser must engage a multitude of additional springs since the 15 pound force would be inadequate resistance to apply an effective exercise workload resistance to the much larger leg muscles. Therefore, the exerciser may manually "hook up" or engage an additional three springs to create a total workload resistance of 60 pounds.

This process of engaging and disengaging one or more springs to vary the workout resistance force throughout a typical Pilates workout comprised of multiple exercises has been practiced since the invention of the first Pilates apparatus nearly a century ago, and is well known to those skilled in the art.

One major deficiency of the resistance-changing process of contemporary Pilates apparatuses is that the process is time-consuming. Pilates classes are typically delivered during a fixed period of time to a group of exercisers, each exercising on their respective apparatuses. It is important for all exercisers to start each of the many exercises together, and at the command of the Pilates instructor. As the instructor calls for a change in exercise, all exercisers must stop, usually dismount the apparatus, quickly change resistance by engaging or disengaging the correct springs, re-mount the apparatus, and ready themselves for the next exercise.

Exercisers with high experience will know what springs to engage or disengage, and do so quickly. Inexperienced exercisers will struggle with the mechanics of changing springs, and will not fully understand color coding related to springs of different K-factors, nor which of the springs to engage or disengage. The inexperienced exerciser will require the personalized assistance of an instructor or fellow exerciser.

As can readily be seen, the act of changing springs between exercises can cause considerable disruption and time delay, significantly diminishing the available workout time available within the time limits of fixed duration class.

Another disadvantage of the traditional spring-changing process is that exercisers are unable to quickly change resistance settings to intensify the workload effort of a given exercise. For instance, at the start of an exercise period, an exerciser would typically "warm up" by performing a number of repetitions of a certain exercise against a comparatively light resistance force. After a few minutes of warming up the working muscles, it would be preferable to increase the resistance to intensify the exercise effort. Traditional Pilates apparatuses do not provide the capability to change the resistance force during the performance of an exercise, and require the exerciser to stop and manually change springs as previously described.

Another disadvantage of contemporary Pilates apparatuses is that exercisers oftentimes simply don't know the appropriate resistance setting for a particular exercise, and inadvertently select too high, or too low of a workload resistance at the start. If the workload resistance is too low, they stop after one or two repetitions, and re-set the springs to a higher workload.

On the other hand, if the set a starting workload resistance that is too high, the exerciser risks injury from overstressing muscles required to overcome the overly high spring resistance force the initially set.

Another disadvantage of contemporary Pilates apparatuses is that all spring settings must be manually adjusted. It is well known in the fitness industry that instructors, throughout the exercise period, frequently instruct the class to change exercises, to increase or decrease the speed at which they should perform the exercises, and change workload levels against which the exercise should be performed. There is presently no ability for an instructor to simultaneously change the workload intensity of all apparatuses of all exercisers in the class. This disadvantage results in a less beneficial workout for the exercisers who otherwise would realize a more intense exercise period.

Yet another significant disadvantage of traditional Pilates apparatuses is the inability of an exerciser to consistently work within a specified cardiovascular performance range. It is well known to those killed in the art of fitness training that exercisers benefit most during an exercise period when the workload intensity throughout the period begins low, ramps up significantly over a period of time, then tapers off as the end of the workout period approaches. During the high intensity period, exercisers may work at 90 percent of their recommended cardiovascular capacity.

Wearable digital activity tracking devices are well known, and are capable of determining an exerciser's cardiovascular levels in real time. As an example, a bicyclist monitoring their performance can use a wearable activity tracking device to determine that they are only working at 50% capacity, and in response, pedal harder until the device indicates that they are working at an 85% capacity.

Unfortunately, even if a Pilates exerciser is using a wearable activity tracking device, Pilates apparatuses all require the exerciser to stop and manually change spring resistance changes in order to intensify workload, thereby disrupting the flow of the exercise routine. Additionally, the stop-and-go process allows the cardiovascular system to momentarily recover, negating many of the physiological benefits realized by continually ramping resistance throughout an exercise routine, thereby continually increasing cardiovascular capacity.

Therefore, those skilled in the art would recognize the significant advantages of a new and novel Pilates apparatus providing for increasing or decreasing workout resistance on demand, and in real-time, without requiring the exerciser to stop the exercise, thereby overcoming the deficiencies of contemporary Pilates apparatuses requiring exercisers to manually change resistance settings.

It will be further appreciated by those skilled in the art that a Pilates apparatus as described would save resistance change-over time during an exercise class, and to the exerciser's delight, allocating more time to beneficial exercise. Delivering more fitness benefits to customers within a given time period is of significant commercial value.

Because of the inherent problems with the related art, there is a need for a new and improved exercise machine adjustable resistance system and method for efficiently varying the workout resistance for an exercise machine.

BRIEF SUMMARY OF THE INVENTION

Provided herein is an exercise machine which includes a control unit in communication with a resistance adjustment system of an exercise machine and a biometric monitoring device used by an exerciser on the exercise machine. The control unit receives biometric data from the biometric monitoring device and sends a control signal to the resistance adjustment system to adjust the resistance of the exercise machine based on the biometric data received.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

Provided herein is an exercise machine adjustable resistance system and method, which comprises a control unit in communication with a resistance adjustment system of an exercise machine and a biometric monitoring device used by an exerciser on the exercise machine. The control unit receives biometric data from the biometric monitoring device and sends a control signal to the resistance adjustment system to adjust the resistance of the exercise machine based on the biometric data received. The resistance of the exercise machine may be adjusted by increasing or decreasing the resistance of a resistance device 3 and/or by increasing or decreasing the incline of the exercise machine with respect to a base (e.g. horizontally align the exercise machine for limited resistance and inclined upwardly from a first end to a second end of the exercise machine for increased resistance). The increase or decrease of the incline of the exercise machine may be accomplished by one or more actuators that elevate the exercise machine accordingly.

The exercise machine of the present invention is preferably comprised of a Pilates exercise machine as illustrated in FIGS. 6 through 8b of the drawings. However, the exercise machine may be comprised of various other types of exercise machines such as, but not limited to, a rowing machine and the like. U.S. Pat. No. 7,803,095 to Sebastien Lagree and U.S. Pat. No. 8,641,585 to Sebastien Lagree illustrate exemplary exercise machines suitable for usage herein and are incorporate by reference in their entirety.

Figure 1:
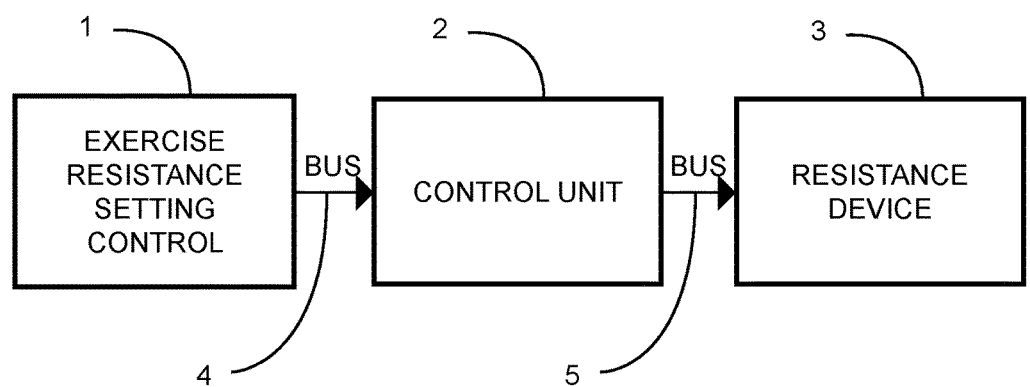
FIG. 1 is an exemplary diagram of a system to electronically control changes in exercise resistance levels of an improved Pilates apparatus.

FIG. 1 is an exemplary diagram of a system to electronically control changes in exercise resistance levels of an improved Pilates apparatus. In FIG. 1, an exercise resistance setting control 1 is an input device for a Pilates exercise adjustment system. An exerciser (not shown) enters the desired level of resistance against which they want to exercise, the signal from the input resistance setting control thereafter being communicated to a control unit 2 by means of a communication control signal bus 4. The bus 4 may be a wireless or wired communication link between the exercise resistance setting control 1 and control unit 2. In its simplest form of function, the control unit 2 processes the input signal so that a control unit 2 output communicates with an resistance device 3 by means of an adjustment system bus 5. The bus 5 may be a wireless or wired communication link between the control unit 2 and resistance device.

It should be noted that the control unit 2 may perform functions beyond the processing of the input control signal, including for example, referencing a table of resistance settings in a database, performing a time-based analysis of differences in resistance settings, or processing signals for displaying resistance levels on a digital display device.

Figure 2:
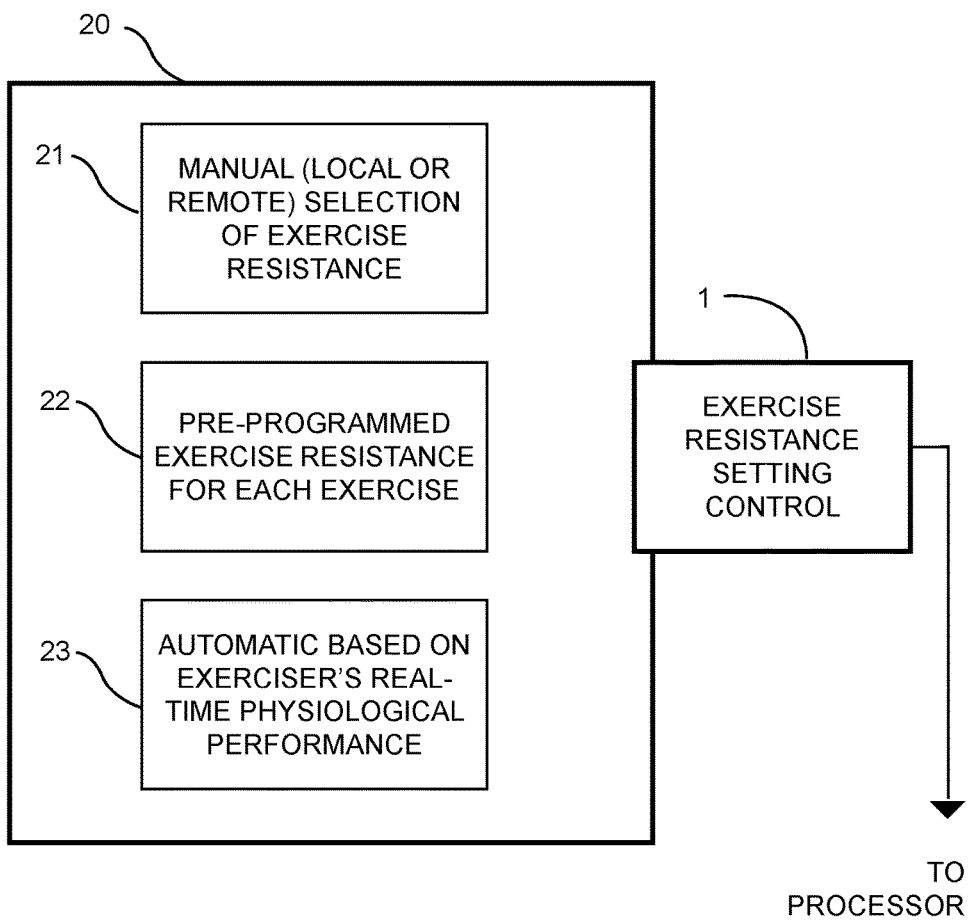
FIG. 2 is an exemplary diagram of various systems and methods of inputting a control signal to control changes in exercise resistance levels of an improved Pilates apparatus.

FIG. 2 is an exemplary diagram of various systems and methods of inputting a control signal that controls changes in exercise resistance levels of an improved Pilates apparatus. In the drawing, an exercise resistance setting control 1 (e.g. a control signal processor) in communication with a control unit 2 originates a control signal from one of many optional control setting sources 20. Signal origination may be generated by an exerciser interfacing with a manual resistance setting control 21, for example, an analog dial, or digital input keypad, whereby an exerciser may specify the desired resistance level, typically expressed in pounds or kilograms.

Further, the control signal may originate from a database of resistance settings shown in the drawing as a preprogrammed resistance setting control 22. Those skilled in the art will appreciate that access to a database would require that a query or instruction first be sent to a database, for instance, a "start" instruction. Although not shown, it would also be well known that a user interface to the database would be required to cause the database to generate a desired control signal.

Still further, a control signal may be caused to be generated by an automatic resistance setting control 23. For example, an exerciser upon the Pilates apparatus may be wearing a heart rate monitor that continually monitors the exerciser's heart rate throughout the exercise period. Although not shown, the heart rate monitor may be in wired or wireless communication with the control unit 2 and database previously discussed. As the signal processor 2 receives a signal indicating that the exerciser's heart rate has changed, the signal processor 2 and database look up the preprogrammed resistance level corresponding to the updated heart rate data, and creates an output signal instructing a resistance level adjustment system to change the resistance level.

It is not the intention of the present invention to limit the control setting source to the examples just discussed. By way of example, the manual resistance setting control 21, preprogrammed resistance setting control 22, and automatic resistance setting control 23, are shown to illustrate the wade range of methods and devices that may be used to originate a control signal that will cause a resistance adjustment system of the present invention to change the resistance level acting on the slidable carriage of a Pilates apparatus at any time that the resistance adjustment system receives the instruction from the signal processor 2.

Figure 3:
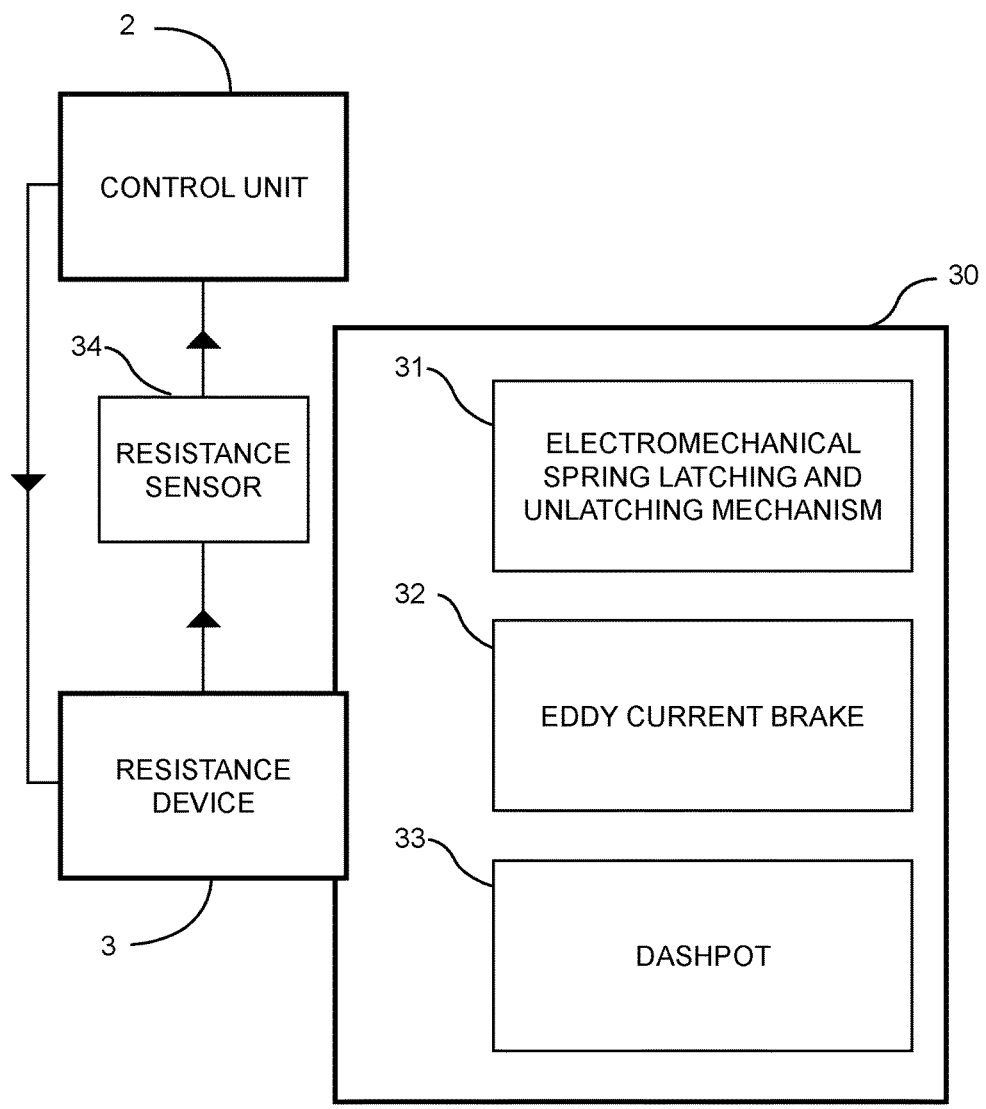
FIG. 3 is an exemplary diagram of various systems and methods of changing resistance levels in response to a resistance control signal of an improved Pilates apparatus.

FIG. 3 is an exemplary diagram of various systems and methods of changing resistance levels in response to a resistance control signal of an improved Pilates apparatus. In the drawing, a resistance device 3 (e.g. exercise resistance adjustment system) receives a signal from a processor 2, such signal directing a change in the resistance level setting of an improved Pilates apparatus. A plurality of resistance variation means 30 are shown, including but not being limited to an electromechanical latching mechanism 31, and eddy current brake 32, a dashpot 33, and a resistance sensing means 34.

In the first example, the resistance adjustment system 3 may comprise an electromechanically actuated latching mechanism 31. Typical Pilates apparatuses provide for removably attachable springs affixed between a fixed end of the apparatus, and a slidable carriage. Exercisers are currently required to stop exercising, dismount the apparatus, and manually engage or disengage one or more springs between the apparatus structure and slidable carriage, thereby increasing or decreasing the resistance workload against which the exerciser must work. The electromechanical latching mechanism 31 of the present invention eliminates the need for an exerciser to manually perform a spring change, and in response to a control signal, automatically actuates a mechanism that latches or unlatches one or more springs between the apparatus structure and slidable carriage. Those skilled in the art will appreciate that a great number of electrically actuated mechanical devices may be used to latch or unlatch a spring from a slidable carriage, including cams, lifters, collets, and other well-known mechanisms. The disclosure of an electromechanical latching and unlatching mechanism is not meant to be limiting, but by way of example, the mechanisms just described illustrate variations of the automatic latching and unlatching system responsive to a control signal of the present invention.

As a second example, the resistance adjustment system 3 may comprise an eddy current brake 32. The use of eddy current brakes 32 in exercise equipment, and specifically on stationary bicycles, is well known. However, eddy current brakes 32 have never before been applied to Pilates apparatuses. Eddy current brakes 32 operate by creating eddy currents through an electromagnetic induction rotor, thereby creating resistance on a coil rotated at high speed between the plates of the rotor. Eddy current brakes 32 may be of a linear structure where a magnetic yolk is used in place of a rotor, and electrical coils located along the length of a rail. U.S. Pat. No. 5,031,900 to Leask discloses an Eddy Current Braking System which is incorporated by reference herein.

One problem with an eddy current brake 32 is that they are generally inefficient at low speeds. Therefore, in the present invention, a rotating eddy current brake 32 may be preferably used when a method of accelerating the rotational speed of a coil in response to force applied by an exerciser on a slidable carriage is used. For example, the slidable carriage may be movably attached to a linear gear, such as a gear rack, interacting with a pinion gear affixed to the rotational shaft of the eddy current brake coil. In such a configuration, a slow linear movement of the slidable carriage, and correspondingly the gear rack, would induce a disproportionately high rotational speed of the coil of the eddy current brake 32.

The braking force of an eddy current brake 32 is changed by varying the current passing through electromagnets. When applied to a novel Pilates apparatus, current changes responsive to one or more control signals received from a control unit 2 during performance of an exercise would change the exerciser's resistance level in real time.

As a third example, variable resistance to a linear exercise force in a Pilates apparatus may be created using a dashpot 33. A dashpot 33 is a term used by those skilled in the art to describe a damper which resists linear motion via friction of a viscous fluid damper, for instance, an hydraulic cylinder. A dashpot 33 generally comprises a cylindrical housing, a piston positioned therein, and a viscous fluid that is moved from one side of the piston to the other through a canal at a controlled velocity proportional to the linear force exerted on the piston ram. The proportional resistance force created by a dashpot 33 acts in a direction opposite to the force and force velocity applied to it. For instance, a dashpot 33 affixed between a stationary end of a Pilates apparatus, and the slidable carriage, would resist the force an exerciser applied to the slidable carriage in a direction opposite to the fixed end of the dashpot 33. The resistance force of the dashpot 33 created by viscous friction may be varied by regulating the size of an orifice, or valve opening, through which the viscous fluid transfers from one side of the piston to the other.

In the present invention, a valve control signal received from the control unit 2 would instruct the valve to open, thereby reducing the friction and resistance level, or to close, thereby increasing the resistance level. Dashpots 33 provide for smooth operation throughout the fluid transfer cycle, an added benefit in Pilates apparatuses that are well known for allowing exercisers to exercise using smooth, low impact motion.

It should be noted that it is not the intention to require the use of ordinary or well known devices or systems just described, nor to limit the use of any these or other known systems or mechanisms to vary exercise resistance in an improved Pilates apparatus, but rather to apply the use of well known resistance control means in response to the resistance control signal of the present invention, thereby causing a real-time resistance change of a Pilates apparatus at any time the control signal is received by the resistance-changing device.

Further, one or more resistance sensing means 34, may be used to measure the resistance force created by the resistance force means, and communicate the level of resistance force to a processor 2 for analysis to determine any required increase or decrease adjustment desired. As an example, a pressure sensor on a dashpot 33 would measure the force applied to the piston, communicating the force level to a processor 2 for analysis of the actual force against the intended force. Thereafter, the processor 2 will send an "open" or "close" signal to the friction valve as a means of respectively decreasing or increasing the resistance level to more closely match the intended resistance level.

Referring to a previously described example of the use of a rotational eddy current brake 32, a rotational shaft strain gauge in communication with the rotational shaft of the eddy current coil may be used to measure the torque applied to the shaft. A processor 2 converting torque measurements into resistance measurements would programmatically determine the instant level of resistance acting upon the slidable carriage, and communicate a signal back to the eddy brake 32 to increase or decrease braking force to thereby change the exercise resistance level in real time.

Figure 4:
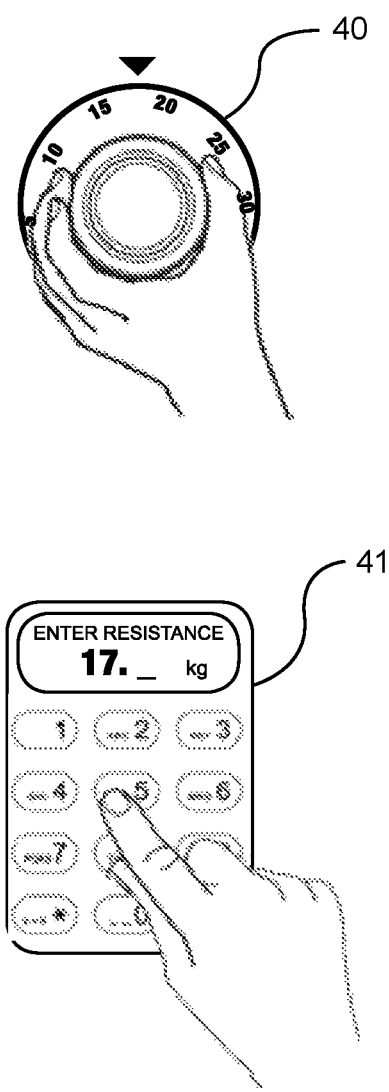
FIG. 4 is an exemplary diagram showing analog and digital control signal input methods.

FIG. 4 is an exemplary diagram showing analog and digital control signal input methods. It is preferable that the system and method of automatically controlling the resistance of an improved Pilates apparatus of the present invention provide a means of inputting a desired resistance level against which to perform an exercise.

Such inputting means may be an analog dial 40, otherwise known to those skilled in the art as an analog electronic dial controller. Analog dials 40 may be indicating, or non-indicating. A non-indicating dial is an inputting device allowing an exerciser to turn the dial to the desires resistance setting without feedback of the actual resistance that has been set, or an indicating dial that receives a signal back from the resistance setting means indicating the actual resistance setting, thereby allowing an exerciser to modify the setting until the desired resistance setting is actually realized.

A digital resistance setting keypad 41, also often referred to as a controller keypad, may be used by an exerciser to input an exercise resistance selection into an improved Pilates apparatus providing for real-time changing of the exercise resistance level of the apparatus at any time throughout the exercise cycle. Controller keypads may use analog keys for inputting a selection, or may incorporate various touch screen technologies to allow for the inputting of one or more resistance settings.

Controller keypads may be non-indicating, meaning that the keypad lacks a display means to indicate the actual resistance setting back to the exerciser after inputting the resistance selection. An indicating keypad may provide for audible or visual information feedback via one or more speakers, or one or more display screens.

The many variations of electronic circuits used in indicating and non-indicating analog dials and controller keypads are well known, and it not the intention of the present invention to require the use of any specific circuit or signal processing means, but rather to illustrate that an analog electronic dial or keypad controllers may be reasonably used as the input device by which an exerciser may input the desired resistance setting of an improved Pilates apparatus.

Figure 5:
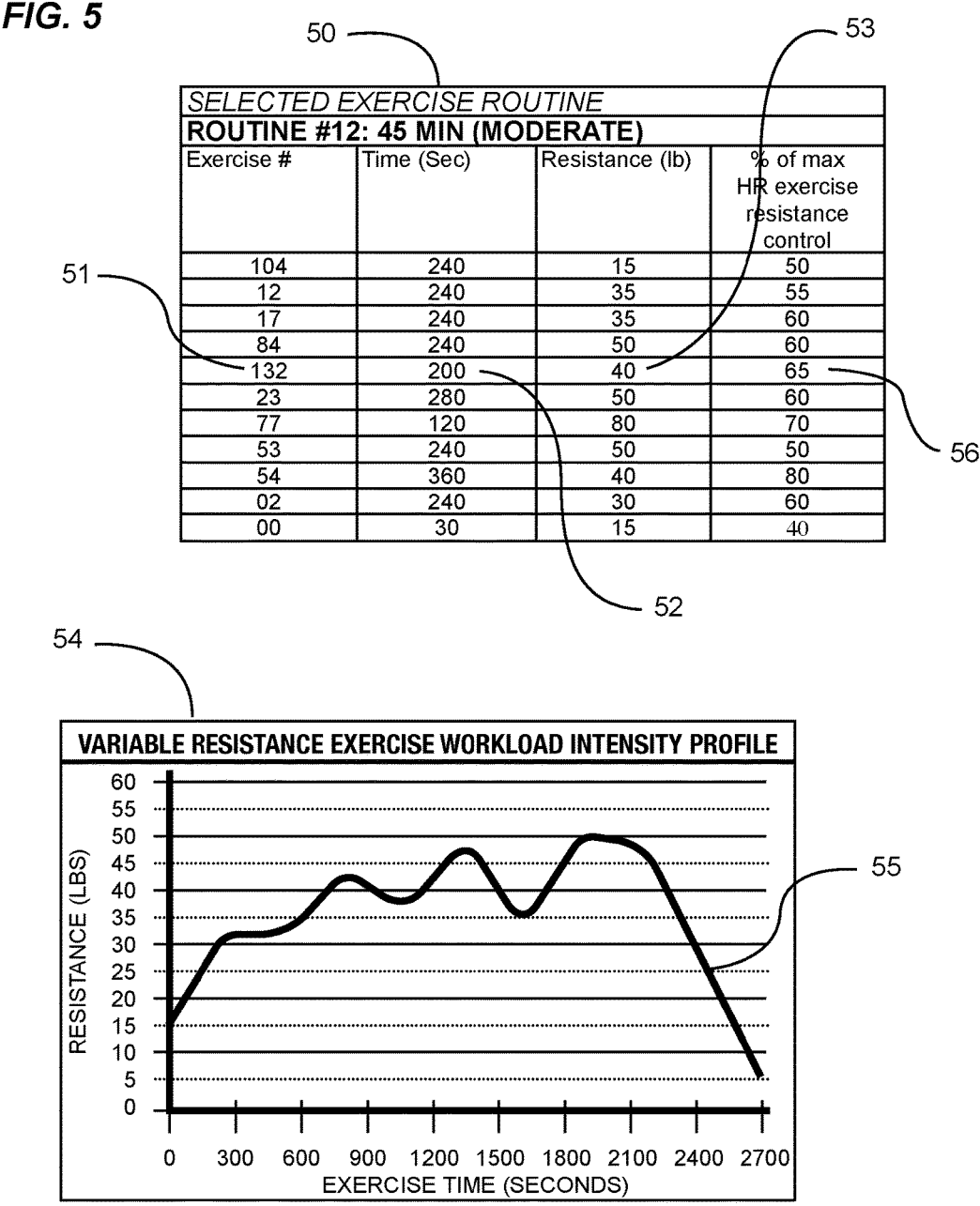
FIG. 5 is an exemplary diagram showing time-related work output of an exerciser based on resistance levels and performance time for a series of Pilates exercises.

FIG. 5 is an exemplary diagram showing time-related work output of an exerciser based on resistance levels and performance time for a series of Pilates exercises.

Exercisers exercising on contemporary Pilates apparatuses are currently provided no method of automatically changing the exercise resistance levels during an exercise sequence performed on a Pilates apparatus. On the other hand, it is well known in the fitness industry that high intensity interval training, often referred to as "HIIT", accelerates weight loss, and increases metabolic function for a longer period of time after completion of an exercise routine.

HIIT requires the exerciser to cyclically vary the intensity of their exercise between moderate intensity, to high intensity, back to moderate or even low intensity, throughout an exercise period. As an example, an runner practicing a HIIT running workout may jog for two minutes, then immediately sprint at a 90 percent of their cardiovascular maximum rate for one minute, then return to jogging for another two minutes, thereafter repeating the cycle until finishing. This more efficient exercise method compares to a runner who may run at a 75 percent of cardiovascular capacity through the exercise period.

Despite the overwhelming body of work validating the advantages of HIIT, the ability of structuring a HIIT routine based on varying the exercise resistance level in real-time, throughout the performance of an exercise routine, has never before been possible on contemporary Pilates apparatuses.

In the drawing, an exerciser may create a program, or select a pre-programmed 45 minute long exercise routine 50 providing for a HIIT-based workout. A typical Pilates routine may include the performance of more than one exercise in a sequence. In a database table containing a list of different Pilates exercises, an exerciser may select a sequence that includes #132 as one exercise number 51, the actual number attributable to any given exercise being arbitrary, other than a designator to differentiate between exercises.

Further, the exerciser may select a time duration 52 (e.g. seconds, minutes, hours) during which to perform the exercise. It should be known that any time duration, or quantification of time, such as seconds or minutes may be used without departing from the system and method of the present invention.

Still further, a designated workload resistance in pounds 53 is selected for the selected exercise and time, thereby completing the time and intensity criteria for the selected exercise. It should be known that any resistance level, or quantification of resistance, such as pounds or kilograms, may be used without departing from the system and method of the present invention.

By continuing the process for inputting exercise, duration and resistance level as just described for additional exercises to be performed during the 45 minute exercise routine, an exerciser on a Pilates apparatus, for the first time, may create an exercise routine that automatically changes the resistance intensity, and the duration of the resistance, for one or more exercises of an exercise routine, without having to stop the routine to manually change resistance settings.

When considering the 45 minute exercise period as a whole, the exercise workload intensity profile 54 will clearly indicate a variation or exercise intensity throughout the period. The workload curve during a routine 55 illustrates a correlation between the workload resistance in pounds, and the performance duration of each exercise performed at the variable workload resistance. The increasing and decreasing points on the workload curve represent cyclical changes from moderate to high intensity exercise as prescribed for HIIT exercise routines.

As is shown in the fourth column, the tale recommends performance of each exercise in the sequence at certain heart rate levels, including a heart rate of 65% of the exerciser's maximum heart rate 56 for exercise 132, as compared to lower heart rates for the exercises immediately preceding and succeeding exercise 132 in the exercise sequence.

Therefore, the present invention, for the first time, provides the advantage of HIIT exercising on an improved Pilates apparatus by automatically changing the exercise workload resistance in real-time, throughout the exercise routine, without the long-accepted tradition of stopping the exercise routine, dismounting the apparatus to manually change spring resistance, remounting the apparatus, and re-starting a new exercise in the exercise routine sequence.

Figure 6:
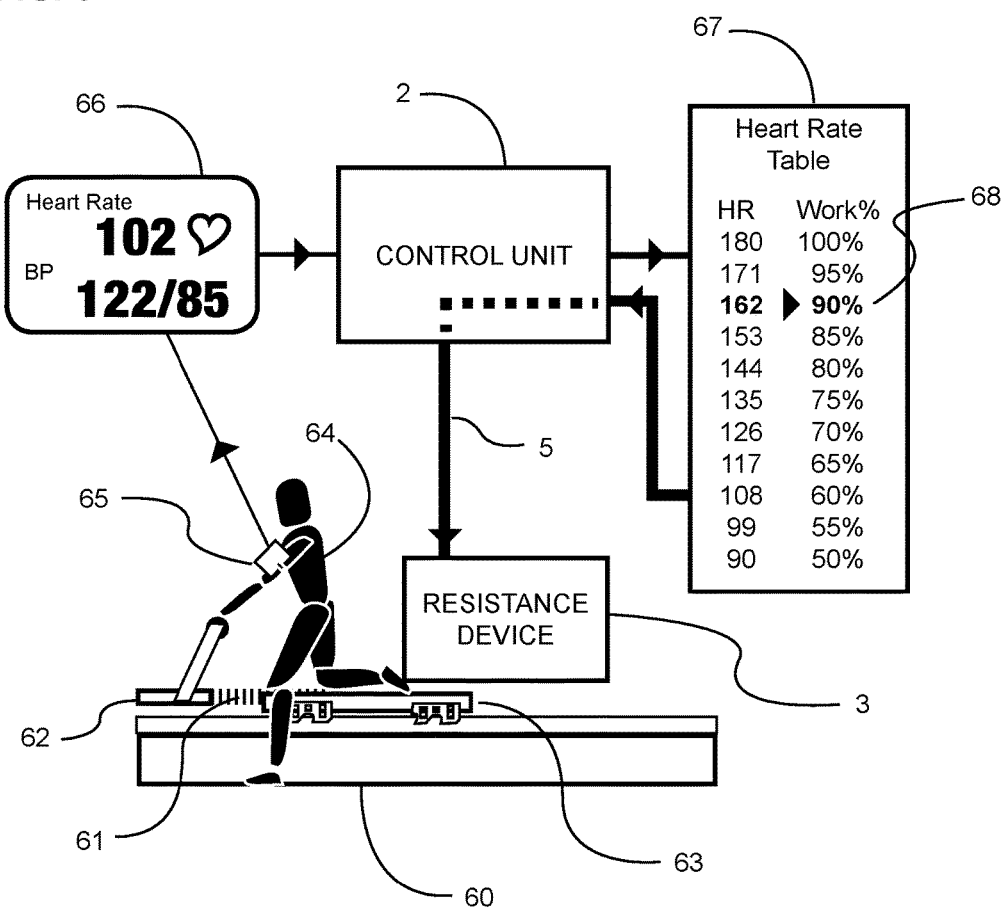
FIG. 6 is an exemplary diagram showing one variation of a system of automatically modifying the resistance levels of a Pilates apparatus in response to the exerciser's cardiovascular performance level.

FIG. 6 is an exemplary diagram showing one variation of a system of automatically modifying the resistance levels of a Pilates apparatus in response to the exerciser's cardiovascular performance level.

In the drawing, a representative exerciser 64 is shown performing an exercise upon a Pilates apparatus 60. The apparatus 60 comprises a substantially stationary structure with a foot end 62, a slidable carriage 63, and one or more resistance springs 61 removably connected between the stationary foot end 62 and slidable carriage 63. The exerciser 64 performs the exercise by using muscle force to overcome the force of the resistance springs 61, thereby moving the slidable carriage in a direction opposite from the foot end 62.

As would be appreciated by those skilled in the art, an exerciser 64 moving the slidable carriage 63 connected to the foot end 62 by a plurality of springs 61 of equal spring tension will expend more energy than an exerciser 64 moving the slidable carriage 63 connected to the foot end 62 with only one spring 61. Therefore, as can readily be realized, by increasing or decreasing the number of springs 61 interconnected between the foot end 62 and slidable carriage 63, an exerciser 64 will respectively increase or decrease the intensity of the fitness workout.

The level of intensity with which an exerciser 64 is performing an exercise is reflected in the exerciser's cardiovascular performance, determined in part by heart rate and blood pressure. By means of a wearable heart rate monitor 65, the exerciser 64 is provided with real-time cardiovascular performance information. In the drawing, the real time heart rate data 66 is shown as 102 beats per minute heart rate, and 122/85 blood pressure.

As a reference point, the maximum heart rate for an individual, and therefore generally considered by those skilled in the art to be equivalent to 100% of an exerciser's heart rate, is often determined by subtracting the exerciser's age from the number 220. Therefore, if the representative exerciser 64 is a 40 year old male, his maximum heart rate could be determined by the formula (220−40)=100% heart rate. The maximum heart rate would therefore be approximately 180 beats per minute.

As can be seen in the heart rate table 67, representative of a heart rate table for a 40 year old male, the 90% target heart rate and work intensity 68 requires the exerciser's heart rate to reach 162 beats per minute. Referring back to the representative actual heart rate 66 of 102 beats per minute, it can be readily determined that the resistance level of the apparatus must increase in order to force the exerciser to work harder, and therefore increase the heart rate to 162.

In the drawing, a wearable heart rate monitor 65 in wired or wireless communication with the electronic resistance adjustment system 3 of the present invention, acts as, or sends a signal to the resistance setting input device not shown. As previously described, the resistance setting input means is in communication with the control unit 2 that will determine the appropriate resistance setting.

The drawing further illustrates one variation of the control signal processor 2 incorporating a database containing one or more heart rate tables 67, and more specifically, a heart rate table 67 representing standard heart rate workloads for a 40 year old male.

Having previously entered, or selected an exercise routine as described in FIG. 5, with the recommended 90% of maximum heart rate selected for the instant exercise being performed by the representative exerciser 64, the control unit 2, in communication with the heart rate table 67, determines that the exerciser 64 is working against too low of a resistance force, and communicates a signal 5 to the resistance adjustment system 3 to increase the resistance level of the apparatus 60.

By actuating one of the previously described mechanisms to automatically adjust the resistance of the Pilates apparatus 60 shown in the drawing, the mechanism will attach one or more additional springs 61 to the slidable carriage 63, thereby increasing the workload, and subsequently the exerciser's heart rate.

In real-time, the wearable heart rate monitor 65 will continually update the control unit 2 of the actual heart rate, and by repeating the process just described, increase or decrease the spring resistance so that the exerciser's heart rate remains at the correct performance level throughout the exercise routine as prescribed by the exerciser's inputted exercise routine program at the beginning of the exercise routine.

Figure 7:
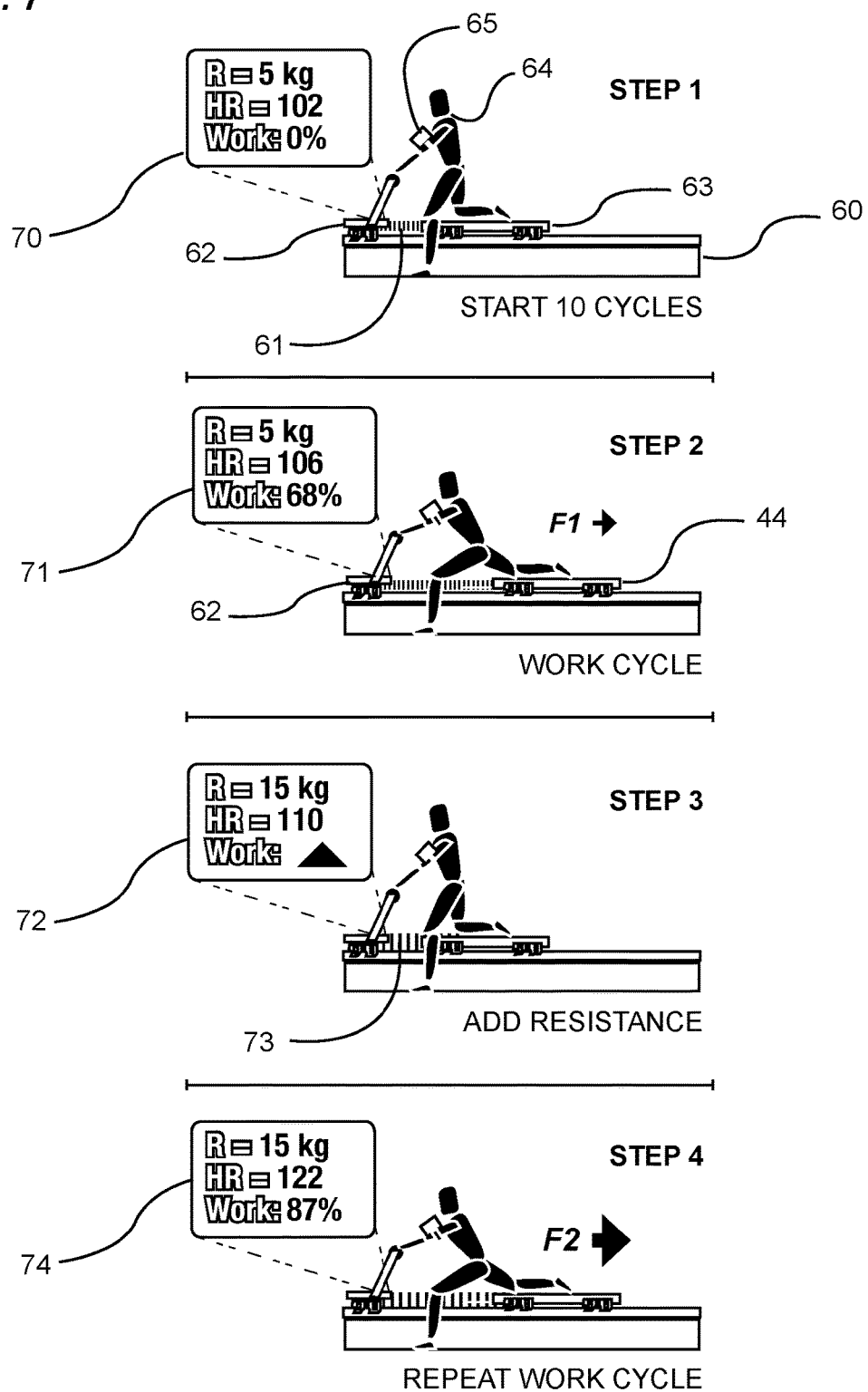
FIG. 7 is an exemplary diagram showing a sequence of illustrations of an exerciser performing multiple repetitions of an exercise upon an improved Pilates apparatus.

FIG. 7 is an exemplary diagram showing a sequence of illustrations of an exerciser performing multiple repetitions of an exercise upon an improved Pilates apparatus.

In the sequence, a simplified sequence shows a representative exerciser 64 performing an exercise upon an improved Pilates apparatus 60 comprising a stationary foot end 62, a slidable carriage 63 and one or more resistance springs 61 removably attachable between the foot end 62 and slidable carriage 63.

In STEP 1, the heart rate data at rest 70 which reflects real-time data received from a wearable heart rate monitor 65 is displayed on a display screen of an improved Pilates apparatus 60 before the exerciser 64 begins exercising.

STEP 2 shows the exerciser 64 after having completed the primary work cycle of the first repetition of ten cycles by exerting a force F1 against the existing resistance setting of the apparatus. As can be readily seen by the information displayed upon the display screen 71, the exerciser's heart rate has increased by 4 beats per minute compared to the resting heart rate 70.

In STEP 3, at the end of the first cycle, the exerciser 64 momentarily stops exercising while transitioning from moving in a direction towards the foot end 62, to moving away from the foot end 62 to start the second cycle of the ten cycles.

The wearable heart rate monitor 65, being in communication with the electronically adjustable resistance system and method of the present invention as previously described, but not shown, immediately determines the heart rate data at rest after first cycle 72 as 110 beats per minute, confirming that increased workload is immediately required in order to quickly get the exerciser's performance up to a higher targeted heart rate. The resistance device 3 responds by attaching one or more additional springs 73 between the foot end 62 of the apparatus 60 and the slidable carriage 63.

STEP 4 shows the exerciser 64 completing the primary workload cycle of the second cycle, this time exerting a higher force F2 against the increased resistance created by the addition of spring tension just described. The display of the heart rate data during second cycle 74 shows that the exerciser's heart rate has increased to 122 beats per minute in response to the automatically increased workload.

Therefore, but understanding the process as generally described in the foregoing sequence, it can be readily appreciated that the new and novel system and method of automatically changing the resistance setting of a Pilates apparatus provides the benefit of establishing and maintaining preferred heart rates corresponding to targeted variable intensity exercises throughout an exercise routine that were never before possible.

Figure 8A:
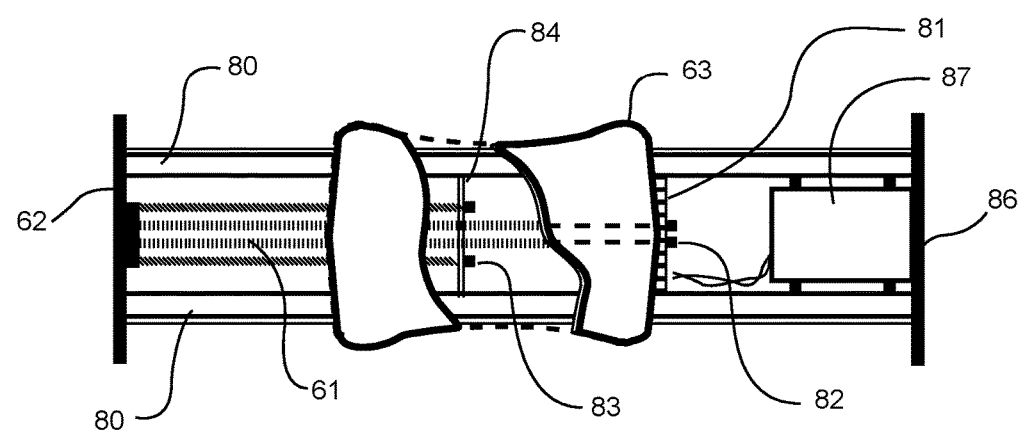
FIG. 8a is an exemplary diagram showing the top view of a first variation of an improved Pilates apparatus.
Figure 8B:
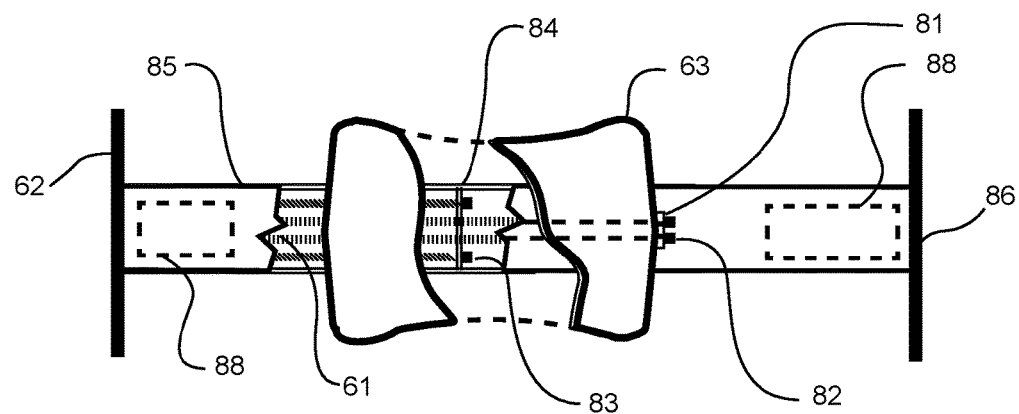
FIG. 8b is an exemplary diagram showing the top view of a second variation of an improved Pilates apparatus.

FIGS. 8a and 8b are exemplary drawings showing the top view of two variations of an improved Pilates apparatus. As will be readily appreciated, the electronically adjustable resistance system 3 and method of the present invention may comprise various electrical, electronic, electromechanical, electromagnetic, and mechanical devices, systems and components not used in traditional Pilates apparatuses. Therefore, accommodations to incorporate the additional components into an improved Pilates apparatus must be reasonably made.

In the top drawing, two parallel sliding rails 80 extend substantially the longitudinal dimension of a Pilates apparatus 60 between the foot end 62 and head end 86. A cut-away top view of a slidable carriage 63 with a spring assembly latch 81 affixed thereto is shown with the pull knobs of engaged spring assemblies 82 removably latched to the springs assembly latch 81.

An spring assembly docking station 84 is shown affixed to the stationary structure, by means of pull knobs of idle spring assemblies 83, retaining two springs 61 not currently latched to the slidable carriage.

An resistance device 3, in response to a signal from a control unit 2 (not shown), provides for latching the pull knobs of one or more idle spring assemblies 83 to the spring assembly catch 81, thereby increasing the resistance force on the slidable carriage 63, and alternatively, in response to a signal from a control unit 2 (not shown), provides for unlatching the pull knobs of one or more pull knobs of engaged spring assembly 82, thereby decreasing the resistance force on the slidable carriage 63.

A component housing 87 is affixed to the structure of a traditional Pilates apparatus 60, the housing 87 containing various components as just described as may be required for any variation of an electronically adjustable resistance system and method of the present invention.

Those skilled in the art will appreciate the importance of minimizing exerciser contact with any of the operational components of an electronically adjustable resistance system thereby minimizing risk of injury to the exerciser 64, as well as minimizing the potential for an exerciser 64 to damage any of the operational components of the system. Therefore, it is preferable to fully enclose as much of the communication, electrical, control, processor and resistance changing means as practicable.

In a variation of an improved Pilates apparatus 60, in the lower drawing, the parallel rails 80 are replaced by an enclosed monorail support for a slidable carriage 85, the enclosed monorail thereby enclosing one or more resistance springs 61, a spring assembly docking station 84 retaining the pull knobs of one or more idle spring assemblies 83, and one or more pull knobs of engaged spring assemblies 82 latched to the springs assembly latch 81.

It should be noted that disclosure of resistance springs 61 is not meant to be limiting, and the enclosed monorail support may house a dashpot 33, eddy current brake 32, or other known means of variably creating a resistance force upon the slidable carriage 63 of a Pilates apparatus 60.

Now, understanding the plurality of components and systems required of the present invention, such components and systems may be mounted and enclosed within the enclosed monorail support for a slidable carriage 85. In FIG. 8b, possible component mounting areas 88 provide for the efficient placement of a plurality of components, including at the opposed ends of the structure of the improved Pilates apparatus 60. More notably, the various resistance inducing means previously described require the use of one or more electrical wires, high pressure hydraulic hoses or plumbing which may be required to traverse substantially the length of the apparatus.

As can be appreciated, running wires, plumbing or hoses substantially the length of a traditional Pilates apparatus 60 would necessarily expose the wires, plumbing or hoses to damage.

Therefore, the advantages of a monorail enclosure to house all of the components of an electronically adjustable resistance system can be immediately recognized by those skilled in the art, and readily appreciated by exercisers 64 using the improved apparatus 60.

Figure 9:
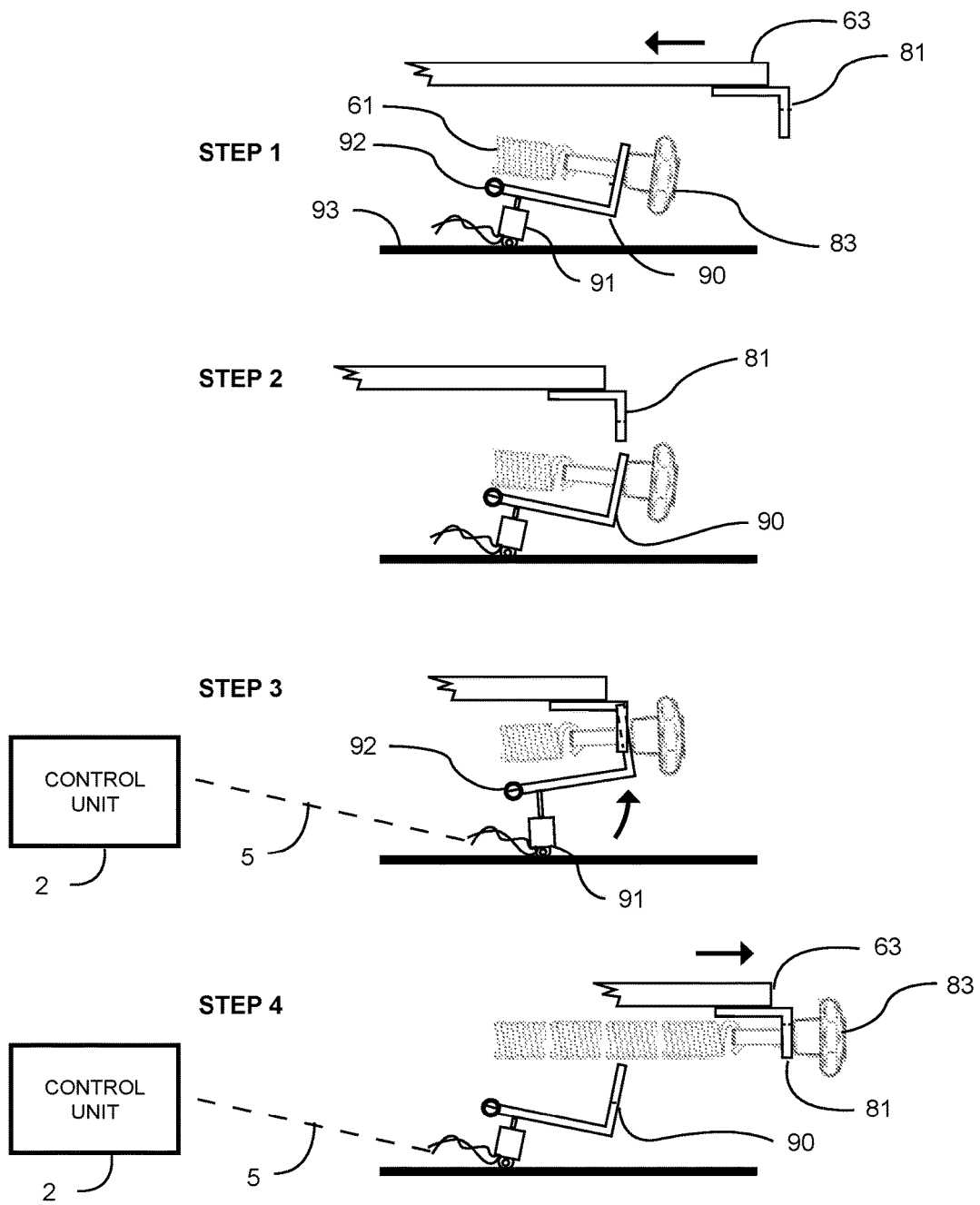
FIG. 9 is an exemplary diagram showing the operation one variation of a system to automatically increase or decrease exercise resistance in real-time during exercise an improved Pilates apparatus.

FIG. 9 is an exemplary diagram showing the operation one variation of a system to automatically increase or decrease exercise resistance in real-time during exercise an improved Pilates apparatus.

More specifically, the drawing illustrates, in four simplified steps, one example of one process of automatically latching a resistance spring assembly between a stationary Pilates structure, and a slidable carriage mounted thereupon.

In STEP 1, a slidable carriage 63 is moved along sliding rails or a monorail. As can be seen, there are no spring assemblies latched to the springs assembly latch 81, and correspondingly no resistance force is applied to the slidable carriage 63. A spring 61 and pull knob 83, together comprising an unlatched, and therefore "idle" spring assembly, is retained by an idle spring assembly carrier 90 affixed to a docking station support structure 93 by means of an axle not shown at the carrier pivoting means 92, and an actuator 91 (e.g. a carrier lifting solenoid). In the drawing, the slidable carriage 63 is being moved linearly in a direction towards the fixed end of the apparatus 60 (not shown).

In STEP 2, the slidable carriage 63 having been moved until it stops with the springs assembly latch 81 being substantially aligned above the idle spring carrier 90, the substantially vertically aligned relationship between the latch 81 and carrier 90 thereby providing for the transfer of the spring assembly from its idle position, to an active position affixed to the assembly latch of the slidable carriage 63.

In STEP 3, in response to a resistance control signal input device (not shown), the control unit 2 communicates a control signal through a bus 5 or wirelessly to a receiver that thereby actuates the actuator 91, pivoting the carrier 90 about the pivoting means 92, until the foot end side of the pull knob is in communication head end surfaces of both the idle spring carrier 90 and the springs assembly latch 81. The lifting of the carrier 90 into a position so that the transfer of the spring assembly from the carrier 90 to the springs assembly latch 81 can be practically instantaneous.

Now, in STEP 4, it can readily be seen that as the slidable carriage 63 moves in a direction opposite from the foot end 62 of the apparatus 60, retention of the pull knob of engaged spring assembly 82 is made by the spring assembly catch of the slidable carriage 63, thereby transferring the force of the spring resistance from the idle spring assembly carrier 90 to the slidable carriage 63.

Further, in response to a control signal 5 from a control unit 2, the actuator 91 lowers the idle spring carrier 90 until such time as a subsequent signal instructs the carrier 90 to lift in order to remove the pull knob 83 from the springs assembly latch 81, thereby reducing the resistance force on the slidable carriage 63.

As will be appreciated by those skilled in the art, the innumerable mechanisms, systems and processes to cause an automatic change of the exercise resistance levels in response to a control input on the improved Pilates apparatus during exercise are not meant to be limiting, and to describe every possible known system or process to accomplish an automatic resistance change would be exhaustive and burdensome, but would nevertheless reinforce the novelty, usefulness and commercial value of the present invention.

Further, it will be appreciated that the electronically adjustable resistance system and method of the present invention, for the first time, provides for more beneficial exercising as a result of eliminating interruptions to an exercise routine to change resistance settings, and more importantly, provides for optimization of the exerciser's exercise time by allowing the exerciser to increase and decrease the HIIT exercise intensity throughout the exercise routine as is well known to those in the fitness industry.

Still further, it will be appreciated by exercisers and Pilates instructors alike, that for the first time, the system and method of the improved Pilates apparatus of the present invention provides for pre-programming different resistances correlating to different Pilates exercises that will be performed in a routine, thereby eliminating the start-stop-re-start sequence between different exercises performed on a traditional Pilates apparatus.

Various aspects of specific embodiments are disclosed in the following description and related drawings. Alternate embodiments may be devised without departing from the spirit or the scope of the present disclosure. Additionally, well-known elements of exemplary embodiments will not be described in detail or will be omitted so as not to obscure relevant details. Further, to facilitate an understanding of the description, a discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the term "embodiments" is not exhaustive and does not require that all embodiments include the discussed feature, advantage or mode of operation.

The word "resistance" is used herein to mean a weight equivalent force that an exerciser upon a Pilates apparatus must overcome in order to move a slidable carriage in a direction opposite to the direction of the force. Resistance in an exercise apparatus may be created by use of springs (including elastic bands, metal springs, plastic springs), viscous fluid dampeners, eddy current brakes, friction blocks, or a variety of other electrical, electromechanical, hydraulic, electromagnetic means well known to those skilled in the art. It is not the objective of the present invention to be limited to known systems or methods of creating a resistance force, but rather to teach a novel method of controlling the resistance force change in an improved Pilates apparatus.

Therefore, as used herein, references may be made to the use of "springs", "brakes" or other methods just described, with no difference in meaning from "resistance". The broadest interpretation of "resistance" inducing methods should be made.

Control circuits are well known to those skilled in the art. It should be noted that it is not the objective of the present invention to limit the architecture or function of a control system of any particular control system design or method, but rather to broadly describe the applicability of control systems when used to change the exercise resistance level of a Pilates apparatus during the performance of an exercise. The broadest interpretation should be given to control systems as they may apply to controlling a variable resistance in an Pilates apparatus.

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. An exercise machine system, comprising:
   an exercise machine having a frame, a moving member movably positioned with respect to the frame and a resistance adjustment device selectively connectable to the moving member, wherein the moving member is movable between a first position and a second position and wherein the resistance adjustment device provides a resistance level to the moving member along at least a first direction of movement of the moving member;
   a biometric monitoring device adapted to be connected to an exerciser, wherein the biometric monitoring device is configured to monitor a biometric state of the exerciser; and
   a control unit in communication with the resistance adjustment device of the exercise machine and the biometric monitoring device, wherein the control unit receives biometric data from the biometric monitoring device relating to the biometric state of the exerciser and wherein the control unit sends a control signal to the resistance adjustment device to adjust the resistance level of the resistance adjustment device based on the biometric data received;
   wherein the resistance adjustment device is comprised of a plurality of resistance devices that are selectively connectable to the moving member, wherein the resistance adjustment device increases a number of the plurality of resistance devices of the resistance adjustment device that are connected to the moving member when the control unit signals an increase in the resistance level and wherein the resistance adjustment device decreases a number of the plurality of resistance devices of the resistance adjustment device that are connected to the moving member when the control unit signals a decrease in the resistance level.

2. The exercise machine system of claim 1, wherein the biometric monitoring device is comprised of a heart rate monitor that measures a heart rate of an exerciser.

3. The exercise machine system of claim 1, wherein the moving member is comprised of a carriage movably positioned upon the frame.

4. The exercise machine system of claim 1, wherein the control unit automatically changes the resistance level of the resistance adjustment device in real-time throughout the exercise routine to achieve a desired biometric state of the exerciser.

5. The exercise machine system of claim 4, wherein the desired biometric state is comprised of a desired percentage of a maximum heartrate for the exerciser.

6. The exercise machine system of claim 5, wherein the control unit increases the resistance level of the resistance adjustment device if a current heartrate of the exerciser is below the desired percentage of the maximum heartrate for the exerciser.

7. The exercise machine system of claim 6, wherein the control unit decreases the resistance level of the resistance adjustment device if a current heartrate of the exerciser is above the desired percentage of the maximum heartrate for the exerciser.

8. The exercise machine system of claim 1, wherein the resistance adjustment device is comprised of an electromechanical latching and unlatching mechanism.

9. The exercise machine system of claim 1, wherein at least one of the plurality of resistance devices is comprised of an eddy current brake.

10. The exercise machine system of claim 1, wherein at least one of the plurality of resistance devices is comprised of a dashpot.

11. The exercise machine system of claim 1, wherein the plurality of resistance devices are each comprised of a spring.

12. The exercise machine system of claim 1, wherein the plurality of resistance devices are each comprised of a brake.

13. The exercise machine system of claim 1, wherein the plurality of resistance devices are electromechanical or electromagnetic.

14. The exercise machine system of claim 1, including a resistance input device in communication with the control unit, wherein the exerciser may manually input a desired resistance level for the resistance adjustment device via the resistance input device.

15. The exercise machine system of claim 1, including a resistance sensor connected to the resistance adjustment device to measure the resistance level, wherein the resistance sensor is in communication with the control unit.

16. A method of using the exercise machine system of claim 1, comprising:
    performing a first exercise on the exercise machine by the exerciser;
    monitoring the biometric state of the exerciser by the biometric monitoring device during the step of performing the first exercise;
    communicating the biometric state of the exerciser to the control unit; and
    adjusting the resistance level based on the biometric state of the exerciser.

17. An exercise machine system, comprising:
    an exercise machine having a frame, a moving member movably positioned with respect to the frame and a resistance adjustment device selectively connectable to the moving member, wherein the moving member is movable between a first position and a second position and wherein the resistance adjustment device provides a resistance level to the moving member along at least a first direction of movement of the moving member;
    a biometric monitoring device adapted to be connected to an exerciser, wherein the biometric monitoring device is configured to monitor a biometric state of the exerciser and wherein the biometric monitoring device is comprised of a heart rate monitor that is configured to measure a heart rate of an exerciser; and
    a control unit in communication with the resistance adjustment device of the exercise machine and the biometric monitoring device;
    wherein the control unit receives biometric data from the biometric monitoring device relating to the biometric state of the exerciser;

wherein the control unit sends a control signal to the resistance adjustment device to adjust the resistance level of the resistance adjustment device based on the biometric data received;

wherein the control unit is configured to automatically change the resistance level of the resistance adjustment device in real-time throughout the exercise routine to achieve a desired biometric state of the exerciser;

wherein the control unit increases the resistance level of the resistance adjustment device if a current heartrate of the exerciser is below the desired percentage of the maximum heartrate for the exerciser and wherein the control unit decreases the resistance level of the resistance adjustment device if a current heartrate of the exerciser is above the desired percentage of the maximum heartrate for the exerciser;

wherein the resistance adjustment device is comprised of a plurality of resistance devices that are selectively connectable to the moving member, wherein the resistance adjustment device increases a number of the plurality of resistance devices of the resistance adjustment device that are connected to the moving member when the control unit signals an increase in the resistance level and wherein the resistance adjustment device decreases a number of the plurality of resistance devices of the resistance adjustment device that are connected to the moving member when the control unit signals a decrease in the resistance level.

18. A method of using the exercise machine system of claim 17, comprising:

performing a first exercise on the exercise machine by the exerciser;

monitoring the biometric state of the exerciser by the biometric monitoring device during the step of performing the first exercise;

communicating the biometric state of the exerciser to the control unit; and adjusting the resistance level based on the biometric state of the exerciser.

19. An exercise machine system, comprising:

an exercise machine having a frame, a moving member movably positioned with respect to the frame and a resistance adjustment device selectively connectable to the moving member, wherein the moving member is movable between a first position and a second position and wherein the resistance adjustment device provides a resistance level to the moving member along at least a first direction of movement of the moving member;

a biometric monitoring device adapted to be connected to an exerciser, wherein the biometric monitoring device is configured to monitor a biometric state of the exerciser and wherein the biometric monitoring device is comprised of a heart rate monitor that is configured to measure a heart rate of an exerciser;

a control unit in communication with the resistance adjustment device of the exercise machine and the biometric monitoring device;

wherein the control unit receives biometric data from the biometric monitoring device relating to the biometric state of the exerciser;

wherein the control unit sends a control signal to the resistance adjustment device to adjust the resistance level of the resistance adjustment device based on the biometric data received;

wherein the control unit is configured to automatically change the resistance level of the resistance adjustment device in real-time throughout the exercise routine to achieve a desired biometric state of the exerciser;

wherein the desired biometric state is comprised of a desired percentage of a maximum heartrate for the exerciser;

wherein the control unit increases the resistance level of the resistance adjustment device if a current heartrate of the exerciser is below the desired percentage of the maximum heartrate for the exerciser and wherein the control unit decreases the resistance level of the resistance adjustment device if a current heartrate of the exerciser is above the desired percentage of the maximum heartrate for the exerciser;

wherein the resistance adjustment device is comprised of a plurality of resistance devices that are selectively connectable to the moving member, wherein the resistance adjustment device increases a number of the plurality of resistance devices of the resistance adjustment device that are connected to the moving member when the control unit signals an increase in the resistance level and wherein the resistance adjustment device decreases a number of the plurality of resistance devices of the resistance adjustment device that are connected to the moving member when the control unit signals a decrease in the resistance level; and a resistance sensor connected to the resistance adjustment device to measure the resistance level, wherein the resistance sensor is in communication with the control unit to provide data relating to the resistance level of the resistance adjustment device to the control unit.

20. A method of using the exercise machine system of claim 19, comprising:

performing a first exercise on the exercise machine by the exerciser;

monitoring the biometric state of the exerciser by the biometric monitoring device during the step of performing the first exercise;

communicating the biometric state of the exerciser to the control unit; and adjusting the resistance level based on the biometric state of the exerciser.

* * * * *